(12) United States Patent
Hayashizaki

(10) Patent No.: US 6,372,437 B2
(45) Date of Patent: *Apr. 16, 2002

(54) METHOD FOR IMPROVING HEAT STABILITY OF RNA

(75) Inventor: Yoshihide Hayashizaki, Ibaraki (JP)

(73) Assignee: The Institute of Physical & Chemical Research, Saitama (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/803,952

(22) Filed: Mar. 13, 2001

Related U.S. Application Data

(62) Division of application No. 09/414,531, filed on Oct. 8, 1999, now Pat. No. 6,221,599, which is a division of application No. 08/899,392, filed on Jul. 23, 1997, now Pat. No. 6,013,488.

(30) Foreign Application Priority Data

Jul. 25, 1996 (JP) .............................. 8-196329
Jul. 25, 1996 (JP) .............................. 8-196331

(51) Int. Cl.$^7$ .......................... C12Q 1/68; C12P 19/34; C07H 21/04
(52) U.S. Cl. ..................... 435/6; 435/91.1; 435/91.2; 536/23.1; 536/24.33; 536/25.3
(58) Field of Search ..................... 435/6, 91.1, 91.2; 536/23.1, 24.33, 25.3

(56) References Cited

U.S. PATENT DOCUMENTS

| | | |
|---|---|---|
| 5,556,771 A | 9/1996 | Shen et al. |
| 5,641,864 A | 6/1997 | Gelfand |
| 5,654,143 A | 8/1997 | Mallet et al. |

FOREIGN PATENT DOCUMENTS

| | | |
|---|---|---|
| DE | 4124286 A | 1/1993 |
| DE | 4411588 | 9/1995 |
| EP | 0035204 | 9/1981 |
| EP | 0569272 A1 | 11/1993 |
| WO | WO91/09944 | 7/1991 |
| WO | WO92/03556 | 3/1992 |
| WO | WO95/14770 | 6/1995 |
| WO | WO95/20682 | 8/1995 |

OTHER PUBLICATIONS

M. Thakar et al., "Osmolyte Mediation of T7 DNA Polymerase and Plasmid DNA Stability", *Biochemistry* 33:12255–12259 (1994).
E. Shimomaye et al., "Use of Avian Myeloblastosis Virus Reverse Transcriptase at High Temperature for Sequence Analysis of Highly Structured RNA", *Gene Anal Techn* 6:25–28 (1989).
R.D. Schmid "Enzyme Stabilization", *Advances in Biochemical Engineering* 12:55–67 (1979).
Gekko et al., "Thermodynamics of Polyol–Induced Thermal Stabilization of Chymotripsinogen" *J. Biochem.* vol. 90, No. 1, 1981 p. 51–58.
Carninci, P. et al., "Thermostabilization and Thermoactivation of Thermolabile Enzymes by Trehalose and its Application for the Synthesis of Full Length cDNA" *Proc. Natl. Acad. Sci. USA*, vol. 95, pp 520–524 (Jan., 1998).
Gray. Chapter 8. Stabilisation of Enzymes with Soluble Additives. In "Thermostability of Enzymes" (Ed. M.N. Gupta), Springer–Verlag, Narosa Publishing House, p. 124–143 (1993).
Katcher, H.. et al, *Bio Techniques* 16(1), pp. 84, 86, 88, 90–92 (1994).
Niemiec, T.M. et al, *Clinical Chemistry* 41 (11) p. 1682 (1995).
Molecular Cloning, A Laboratory Manual, 2d Ed., Sambrook et al., Cold Spring Harbor Laboratory Press, Plainview NY, 1989, pp. 14, 14–14.17.

*Primary Examiner*—Sean McGarry
*Assistant Examiner*—Mark L. Shibuya
(74) *Attorney, Agent, or Firm*—Burns, Doane, Swecker & Mathis, LLP

(57) ABSTRACT

A method for preparing a CDNA from a mRNA using a reverse transcriptase wherein reverse transcription is performed at a temperature at which the mRNA does not take a secondary structure, for example, at a temperature of 45° C. or more. The method is performed, for example, using a heat-labile reverse transcriptase in the presence of a substance exhibiting chaperone function having chaperone function such as saccharides. The method is performed, for example, in the presence of metal ions necessary for activation of the reverse transcriptase and a chelating agent for the metal ions such as a deoxynucleotide triphosphate. The method is capable of reverse transcription over the full length of mRNA template even if the mRNA is a long chain mRNA and, as a result, producing a full length cDNA.

6 Claims, 2 Drawing Sheets

METHOD FOR IMPROVING HEAT STABILITY OF RNA

This application is a divisional, of application No. 09/414,531, filed Oct. 8, 1999, now U.S. Pat. No. 6,221,599, which is a divisional of Ser. No. 08/899,392, filed Jul. 23, 1997 now U.S. Pat. No. 6,013,488.

BACKGROUND OF THE INVENTION

1. Field of the Invention

The present invention relates to a method for reverse transcription which can produce a full length cDNA from a mRNA. In addition, the present invention relates to a method for improving heat stability of RNA.

2. Related Art

It is known that cDNAs can be obtained from mRNAs in vitro using a reverse transcriptase (RNA-dependent DNA polymerase). A project elucidating whole human gene sequences is moving on and, in that project, mRNA strands are produced by using genes as templates and full length cDNA strands are produced in turn by using the mRNA strands as templates. That is, synthesis of first chains of cDNA from mRNA strands is used as a first step of production of cDNA libraries, RT-PCR and the like.

Reverse transcription is utilized in order to obtain full length cDNA strands from the mRNAs as described above. However, conventional reverse transcription can not afford full length cDNAs from mRNAs because the conventional reverse transcription method could not complete reverse transcription to the most end cap site of mRNAs.

According to the present inventor's examination, it was found that the failure of complete reverse transcription is caused as follows. That is, a long chain mRNA may form a secondary structure like secondary structure of protein and the elongation by reverse transcriptase is sterically hindered at the site forming the secondary structure. As a result, reverse transcription was not completed to the end of mRNA.

That is, current techniques for reverse transcription have a technical limitation that the reaction is ended prematurely because of a stable secondary structure of mRNA and thus the probability of complete transcription over the whole transcription unit including its 5' end is extremely low. This technical limitation affects the quality of libraries. That is, most of cloned cDNAs synthesized from the poly A at the 3' end using an oligo dT as a primer have only the 3' end and do not have the full length because of the premature termination of the synthesis. Several attempts have been made to overcome this problem. For example, it was proposed that the mRNAs are pre-treated at 70° C. to unfold the secondary structure before the synthesis of the first chains. It is also possible to treat the mRNAs with methylmercury hydroxide instead of the heat treatment. Though these techniques are effective for increasing efficiency of the synthesis of the first chain to some extent, they are not yet sufficient to efficiently obtain full length cDNAs. In particular, they show particularly low efficiency for the reverse transcription of long mRNAs of several kbp or more.

Therefore, the first object of the present invention is to provide a method capable of reverse transcription of mRNA over the full length and hence capable of providing a full length cDNA even if a long chain mRNA is used as a template.

In this respect, the present inventor has found that the above first object of the present invention can be achieved by performing reverse transcription at a temperature at which mRNA does not form a secondary structure. Though the temperature range where mRNAs do not form a secondary structure may change depending on buffer composition and the like, it is for example a range of 45° C. or more, especially, 60° C. or more.

In such a temperature range, mRNAs can be maintained in a condition that it does not take the secondary structure and the synthesis of the first chain can be effected efficiently. However, it was also found that, in such a temperature range as mentioned above, (1) the reverse transcriptase may be disadvantageously inactivated depending on the kind of the enzyme, and (2) stability of mRNA may be disadvantageously deteriorated (mRNA is fragmented) when metal ions necessary for activation of reverse transcriptase such as magnesium ions and a buffer agent such as Tris [Tris (hydroxymethyl)aminomethane] are present simultaneously.

Therefore, the second object of the present invention is to provide a method which is capable of reverse transcription of mRNA over the full length of the mRNA even if a long chain mRNA is used as a template by performing the reverse transcription of mRNA at a temperature at which the mRNA does not form the secondary structure and, in addition, which can prevent inactivation of the enzyme by heat, i.e., activate it at an elevated temperature even when a heat-labile reverse transcriptase is used and, as a result, provide a full length cDNA with high reliability.

The third object of the present invention is to provide a method which is capable of reverse transcription of mRNA over the full length of mRNA even if a long chain mRNA is used as a template by performing the reverse transcription of mRNA at a temperature at which the mRNA does not form the secondary structure and, in addition, which can provide a full length cDNA with high reliability by using a heat-resistant reverse transcriptase.

The fourth object of the present invention is to provide a method which is capable of reverse transcription of mRNA over the full length of mRNA even if a long chain mRNA is used as a template by performing the reverse transcription of mRNA at a temperature at which the mRNA does not form the secondary structure and, in addition, which can maintain stability of mRNA and hence provide a full length cDNA with high reliability even when metal ions necessary for activation of reverse transcriptase is present, in particular, when a buffer agent such as Tris is further present simultaneously.

The fifth object of the present invention is to provide a method improve heat stability of mRNA even when metal ions necessary for activation of reverse transcriptase is present, in particular, when a buffer agent such as Tris is further present simultaneously.

SUMMARY OF THE INVENTION

As the first embodiment of the present invention, which can achieve the above first object of the present invention, there is provided a method for preparing a cDNA from a mRNA using a reverse transcriptase wherein reverse transcription is performed at a temperature at which temperature the mRNA does not take a secondary structure.

As the second embodiment of the present invention, which can achieve the above second object of the present invention, there is provided a method for preparing a cDNA from a mRNA using a reverse transcriptase wherein reverse transcription is performed at a temperature at which the mRNA does not take a secondary structure using a heat-labile reverse transcriptase in the presence of a substance exhibiting chaperone function.

As the third embodiment of the present invention, which can achieve the above third object of the present invention, there is provided a method for preparing a cDNA from a mRNA using a reverse transcriptase wherein reverse transcription is performed at a temperature at which the mRNA does not take a secondary structure using a heat-resistant reverse transcriptase.

As the fourth embodiment of the present invention, which can achieve the above fourth object of the present invention, there is provided a method for preparing a cDNA from a mRNA using a reverse transcriptase wherein reverse transcription is performed at a temperature at which the mRNA does not take a secondary structure in the presence of metal ions necessary for activation of reverse transcriptase, a Tris buffer and a chelating agent for the metal ions.

As the fifth embodiment of the present invention, which can achieve the above fifth object of the present invention, there is provided a method for improving heat stability of RNAs in a solution containing metal ions wherein the solution further contains a chelating agent for the metal ions.

One of the preferred embodiments of the invention is a method for preparing a cDNA from a mRNA using a reverse transcriptase wherein:

(1) the reverse transcription is performed at a temperature at which the mRNA does not take a secondary structure, (2) the reverse transcription is performed using a heat-labile reverse transcriptase in the presence of one or more substances exhibiting chaperone function, and (3) the reverse transcription is performed in the presence of metal ions necessary for activation of the reverse transcriptase and a chelating agent for the metal ions.

Another preferred embodiment of the invention is a method for preparing a cDNA from a mRNA using a reverse transcriptase wherein:

(1) the reverse transcription is performed at a temperature at which the mRNA does not take a secondary structure, (2) the reverse transcription is performed using a heat-labile reverse transcriptase in the presence of one or more substances exhibiting chaperone function and one or more polyalcohols, and (3) the reverse transcription is performed in the presence of metal ions necessary for activation of the reverse transcriptase and a chelating agent for the metal ions.

DETAILED DESCRIPTION OF THE INVENTION

Figure 1:
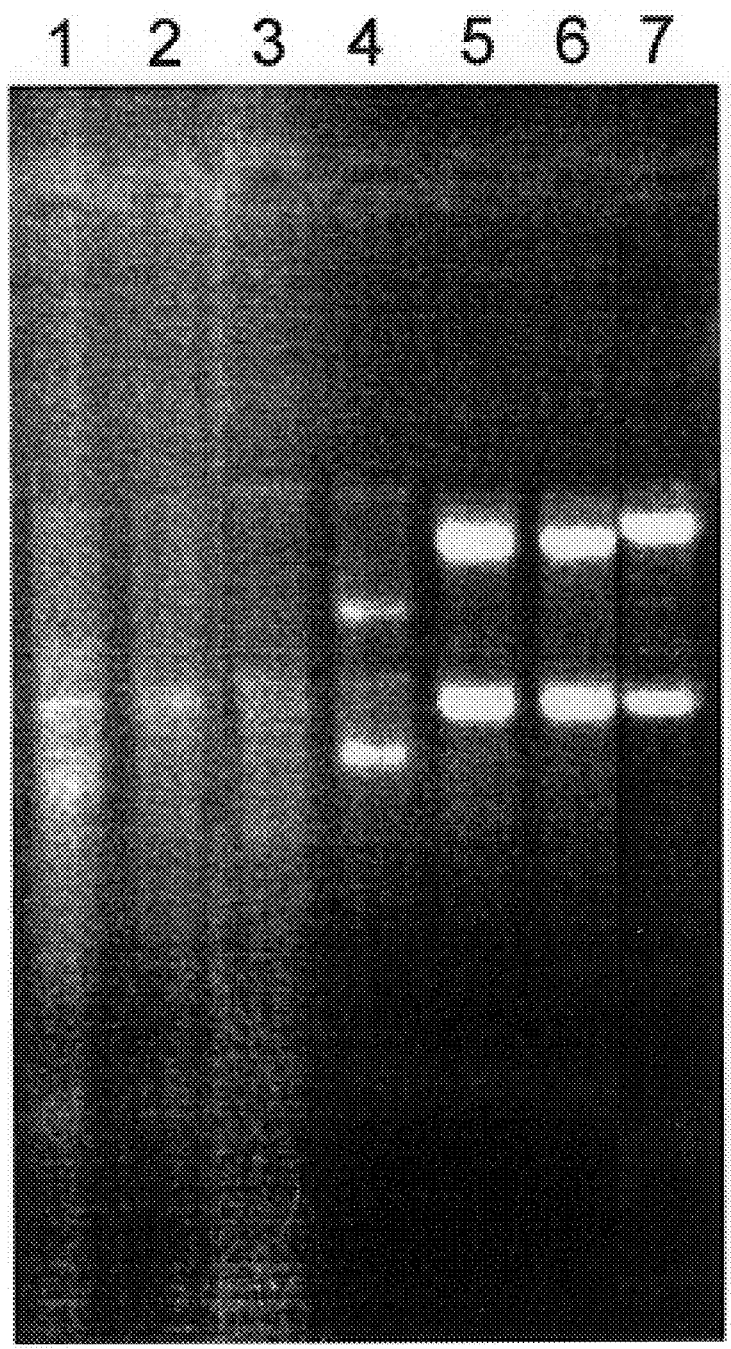
FIG. 1 is a photograph showing the results of agarose gel electrophoresis obtained in Example 1.

The first embodiment of the method for preparing a cDNA from a mRNA using a reverse transcriptase according to the present invention is characterized in that the reverse transcription is performed at a temperature at which the mRNA does not take a secondary structure. The "temperature at which the mRNA does not take a secondary structure" means, for example, a temperature of 45° C. or more, more precisely, a temperature in the range of 45–90° C. As the temperature becomes higher, it becomes easier to keep the mRNA not taking a secondary structure, but the activity of reverse transcriptase and the stability of the mRNA tend to be deteriorated. Therefore, the temperature is preferably in the range of 50–75° C.

The chain length of the mRNA used for the method of the present invention is not particularly limited. However, it is considered unnecessary to use the present invention for a short chain mRNA which does not take a secondary structure, whereas it is difficult to obtain reverse transcription producing a full length cDNA as to a mRNA of 4 kbp or more, in particular, 7 kbp or more. Therefore, from this point of view, the method of the present invention is particularly useful for the reverse transcription of a mRNA of 4 kbp ore more, in particular, 7 kbp or more. However, a mRNA of less than 4 kbp is not excluded from the objective of the present invention.

The second embodiment of the method for preparing a CDNA from a mRNA using a reverse transcriptase according to the present invention is characterized in that it uses a heat-labile reverse transcriptase and the reverse transcription is performed in the presence of a substance exhibiting chaperone function.

In the present invention, the heat-labile reverse transcriptase means a reverse transcriptase exhibiting an optimum temperature of 45° C. or lower. Examples of such a heat-labile reverse transcriptase include Superscript II, AMV reverse transcriptase, MuLV reverse transcriptase and the like, but it is not limited to these.

A reverse transcriptase usually used at an ordinary temperature such as Superscript II exhibits a lower activity at a temperature of 45° C. or more compared to the activity at the optimum temperature and exhibits substantially no activity at a temperature higher than a certain level. Further, if such a reverse transcriptase is maintained at a temperature of 50° C. or higher for a certain period of time, it no longer exhibits the activity even though it is returned to room temperature.

In particular, when the chain length of mRNA is long, the reverse transcription is likely to prematurely terminate before a complete cDNA is synthesized because of inactivation of the enzyme by heat and hence full length transcription becomes difficult. Therefore, according to the present invention, a substance exhibiting chaperone function is added to the reverse transcription system so that the activity of the reverse transcriptase can be maintained even at an elevated temperature (it is possible to prevent reduction of the activity and inactivation by heat).

Examples of the substance exhibiting chaperone function include saccharides, amino acids, polyalcohols and their derivatives, and chaperone proteins. However, the substance is not limited to these. The "chaperone function" means a function for renaturing proteins denatured by stress such as heat shock, or a function for preventing complete denaturation of proteins by heat to maintain the native structure.

Examples of the saccharide exhibiting the chaperone function include oligosaccharides and monosaccharides such as trehalose, maltose, glucose, sucrose, lactose, xylobiose, agarobiose, cellobiose, levanbiose, quitobiose, 2-β-glucuronosylglucuronic acid, allose, altrose, galactose, gulose, idose, mannose, talose, sorbitol, levulose, xylitol and arabitol. However, the saccharide is not limited to these. Those saccharides mentioned above can be used alone or in any combination thereof. Among these, trehalose, sorbitol, xylitol, levulose and arabitol exhibit strong chaperone function and marked effect for activating enzymes at an elevated temperature.

Examples of the amino acids and derivatives thereof include $N^\epsilon$-acetyl-β-lysine, alanine, γ-aminobutyric acid, betain, N $^\alpha$-carbamoyl-L-glutamine 1-amide, choline, dimethylthetine, ecotine (1,4,5,6-tetrahydro-2-methyl-4-pirymidine carboxilic acid), glutamate, β-glutammine, glycine, octopine, proline, sarcosine, taurine and trymethylamine N-oxide (TMAO). However, the amino acids and derivatives thereof are not limited to these. Those amino acids mentioned above can be used alone or in any combination thereof. Among these, betain and sarcosine exhibit strong chaperone function and marked effect for activating enzymes at an elevated temperature.

The substance exhibiting chaperone function include polyalcohols. The saccharides are included in polyalcohols and other examples of the polyalcohols include glycerol, ethylene glycol, polyethylene glycol and the like. Those polyalcohols can be used alone or in any combination thereof.

The substance exhibiting chaperone function include chaperone proteins. Examples of the chaperone proteins include chaperone proteins of Thermophiric bacteria and heat shock proteins such as HSP 90, HSP 70 and HSP 60. Those chaperone proteins can be used alone or in any combination thereof.

These substances exhibiting chaperone function show different optimum concentrations for stabilizing the enzyme depending on the kind of the enzyme and the optimum concentration may vary among the substances for the same enzyme. Therefore, a concentration of particular substance to be added to a specific reaction system may be suitably decided depending on the kinds of the substance and the enzyme such as reverse transcriptase.

To enhance the effect of the substances exhibiting chaperone function such as saccharides, amino acids or chaperone proteins, one or more kinds of polyalcohols may be used in addition to one ore more kinds of the above substances. Examples of the polyalcohol include glycerol, ethylene glycol, polyethylene glycol and the like.

The third embodiment of the method for preparing a cDNA from a mRNA using a reverse transcriptase according to the present invention is characterized in that it is carried out by using a heat-resistant reverse transcriptase.

In the present invention, a heat-resistant reverse transcriptase refers to a reverse transcriptase having an optimum temperature of about 40° C. or more. Examples of such a heat-resistant reverse transcriptase include Tth polymerase, but the heat-resistant reverse transcriptase is not limited to this.

Tth polymerase shows an optimum temperature of 70° C. and can catalyze the reverse transcription with a high activity in the above temperature range of 45° C. or higher.

The fourth embodiment of the method for preparing a cDNA from a mRNA using a reverse transcriptase according to the present invention is characterized in that, when the reverse transcription is performed in the presence of the metal ions necessary for activating the reverse transcriptase, a chelating agent for the metal ions is used simultaneously.

Enzymes may require metal ions for their activation. For example, Superscript II, which is a reverse transcriptase, requires magnesium ions for its activation. However, in a buffer containing magnesium ions such as a Tris buffer, fragmentation of mRNAs may proceed under the temperature condition mentioned above and hence it is difficult to obtain full length cDNAs. Likewise, Tth polymerase requires manganese ions as metal ions for its activation. However, also in a buffer containing manganese ions such as a Tris buffer, fragmentation of mRNA may actively proceed under the temperature condition as mentioned above and hence it is difficult to obtain full length cDNAs.

To solve this problem, according to the method of the present invention, a chelating agent for metal ions is added to the system so that the activity of reverse transcriptase should be maintained and the fragmentation of mRNAs can be prevented. However, if all of the metal ions necessary for the activation of the reverse transcriptase are chelated, the reverse transcriptase loses its activity. Therefore, it is suitable to use a chelating agent of comparatively weak chelating power.

Examples of such a chelating agent of comparatively weak chelating power include deoxynucleotide triphosphates (dNTPs). The chelating agent of comparatively weak chelating power is suitably used in an approximately equimolar amount of the metal ion. When a deoxynucleotide triphosphate is used as the chelating agent, for example, it is suitable to add an approximately equimolar amount of deoxynucleotide triphosphate as to the metal ion. Accordingly, the amount of the chelating agent can be suitably decided with consideration to the chelating power as to the objective metal ion, so that the reverse transcriptase activity can be maintained and the fragmentation of mRNAs can be prevented. The deoxynucleotide triphosphates, dATP, dGTP, dCTP and dTTP, may be used alone or in any combination thereof. All of the four kinds of dNTPs, dATP, dGTP, dCTP and dTTP, may be used together. Since these can serve also as substrates of the reverse transcription, all of them are usually used together.

A preferred, but non-limitative embodiment of the method for preparing a cDNA from a mRNA using reverse transcriptase according to the present invention is a method characterized in that:

(1) the reverse transcription is performed at a temperature at which the mRNA does not take a secondary structure, for example, a temperature of 45 to 90° C., particularly preferably a temperature of around 60° C., (2) the reverse transcription is performed in the presence of one or more substances exhibiting chaperone function and one or more polyalcohols, and (3) the reverse transcription is performed in the presence of metal ions necessary for activation of the reverse transcriptase and a chelating agent for the metal ions.

For example, the method is performed by using Seperscript II as the reverse transcriptase in a Tris buffer containing deoxynucleotide triphosphates as the chelating agents and magnesium ions.

The fifth embodiment of the present invention which is a method for improving heat stability of RNAs in a solution containing metal ions is characterized in that the solution further contains a chelating agent for the metal ions.

As mentioned above, enzymes may require metal ions for their activation and in a Tris buffer containing metal ions such as magnesium ions, fragmentation of mRNAs may proceed under an elevated temperature. In the fifth embodiment of the present invention, a chelating agent for the metal ions is added to a solution containing RNAs for improvement of heat stability.

A chelating agent for metal ions is added to the solution so that the fragmentation of mRNAs can be prevented and if reverse transcriptase coexists, the activity of reverse transcriptase should also be maintained. However, if all of the metal ions necessary for the activation of the reverse transcriptase are chelated, the reverse transcriptase may lose its activity. Therefore, it is suitable to use a chelating agent of comparatively weak chelating power.

Examples of such a chelating agent of comparatively weak chelating power include deoxynucleotide triphosphates (dNTPs). The chelating agent of comparatively weak chelating power is suitably used in an approximately equimolar amount of the metal ion. When a deoxynucleotide triphosphate is used as the chelating agent, for example, it is suitable to add an approximately equimolar amount of deoxynucleotide triphosphate as to the metal ion.

Accordingly, the amount of the chelating agent can be suitably decided with consideration to the chelating power as to the objective metal ion, so that the reverse transcriptase activity can be maintained and the fragmentation of mRNAs can be prevented. The deoxynucleotide triphosphates, DATP, dGTP, dCTP and dTTP, may be used alone or in any combination thereof. All of the four kinds of dNTPs, DATP, dGTP, dCTP and dTTP, may be used together. Since these can serve also as substrates of the reverse transcription, all of them are usually used together.

The solution containing RNAs can further contain one or more polyalcohols such as glycerol.

According to the fifth embodiment of the present invention, heat stability of RNAs is improved even though the an RNA containing solution further contains metal ions such as magnesium ions or manganese ions and/or tris (hydroxymethyl)aminomethane. In addition, the above improvement is obtainable, for example, at a temperature of 40–100° C., preferably 45–90° C.

EXAMPLES

The present invention will be further explained in detail with reference to the following examples.

Example 1
Stability of mRNA in metal ion-containing buffer optionally containing dNTP To examine stability of RNAs in a buffer (50 mM Tris, pH 8.3, 3 mM $MgCl_2$) containing several additives, total River RNAs were incubated in various buffer solutions of the compositions listed below.

TABLE 1

| Lane | |
|---|---|
| 1 | 50 mM Tris, pH 8.3, 3 mM $MgCl_2$, 15% (v/v) glycerol |
| 2 | 50 mM Tris, pH 8.3, 3 mM $MgCl_2$ |
| 3 | 50 mM Tris, pH 8.3, 3 mM $MgCl_2$, 2 mM dNTP |
| 4 | 50 mM Tris, pH 8.3, 3 mM $MgCl_2$, 3 mM dNTP |
| 5 | 50 mM Tris, pH 8.3, 3 mM $MgCl_2$, 4 mM dNTP |
| 6 | 50 mM Tris, pH 8.3, 3 mM $MgCl_2$, 3 mM dNTP, 15% glycerol |
| 7 | Sterilized water |

To visualize fragmentation of RNAs after the incubation, the samples were subjected to agarose gel electrophoresis as described by Sambrook (Molecular Cloning, The second edition pp. 7.43–7.45). The gel was stained with ethidium bromide and the degree of the RNA fragmentation was evaluated by comparing relative band intensities of rRNA. The results of the agarose gel electrophoresis are shown in FIG. 1 (Lanes 1-7).

As shown in Lane 1, the RNAs were not sufficiently protected from the fragmentation by glycerol in the presence of magnesium ion (free $Mg^{2+}$) of high concentration, i.e., when incubated in 50 mM Tris, pH 8.3, 3 mM $MgCl_2$, 15% (v/v) glycerol. In fact, the degree of the fragmentation was similar to that obtained in 50 mM Tris, pH 8.3, 3 mM $MgCl_2$ in the absence of glycerol (Lane 2).

As shown in Lane 3, the fragmentation of RNA was not prevented yet by treatment with 50 mM Tris, pH 8.3, 3 mM $MgCl_2$, 2 mM dNTP.

On the other hand, the fragmentation of RNA was partially prevented in the condition of 50 mM Tris, pH 8.3, 3 mM $MgCl_2$, 3 mM dNTP (same molar concentrations of $Mg^{2+}$ and NTP) as shown in Lane 4.

Further, as shown in Lane 5, in 50 mM Tris, pH 8.3, 3 mM $MgCl_2$, 4 mM dNTP, i.e., in a condition that the concentration of NTP was higher than that of $Mg^{2+}$ by 1 mM, the RNAs were very stable. However, it was also found that the activity of the reverse transcriptase is reduced under this condition.

So, 15% glycerol was added to 50 mM Tris, pH 8.3, 3 mM $MgCl_2$, 3 mM dNTP (same molar concentrations of NTP and $Mg^{2+}$) and the RNAs did not undergo fragmentation under this condition as shown in Lane 6. It was also found in a separate experiment that the activity of reverse transcriptase was completely maintained under this condition.

Under the condition of Lane 6, stability of the RNAs was almost similar to that obtained in Lane 7, i.e., in sterilized water.

Example 2
Improvement of reverse transcription efficiency by making reverse transcriptase heat-resistant To examine reverse transcription activity under the novel condition of Lane 6, cDNAs were synthesized using RNAs as template. The RNAs were transcribed in vitro by T7 RNA polymerase as mentioned below. The RNAs were prepared by transcribing pBluescript II SK, which had been cleaved into a linear form with a restriction enzyme NotI, in vitro with T7 RNA polymerase. This reaction was initiated from T7 promoter described in the instruction of pBluescript II SK.

The resulting products were evaluated. By using RNAs as a template transcribed in vitro and evaluating the products by electrophoresis, reverse transcription efficiencies of the samples can be compared with one another and thereby non-specific transcription termination which leads to premature termination of reverse transcription and/or reduction of reaction efficiency can be evaluated.

As a control, the following standard buffer condition was used: 50 mM Tris-HCl, pH 8.3, 75 mM KCl, 3 mM $MgCl_2$, 10 mM dithiothreitol, 0.75 mM each of dNTPs (DATP, dGTP, dCTP and dTTP).

In the above standard buffer condition, 1 µg of template RNA, 400 ng of primer (20mer SK primer, CGCTCTAGAACTAGTGGATC) and 200 units of Superscript II were prepared and the final volume was adjusted to 20 µl. 0.2 µl of [α-$^{32}$P]dGTP was used for labeling of reverse transcription products. The RNA and the primer were incubated at 65° C. before the other substrates were added. Then, the reaction was performed at 42° C. for 1 hour. The reaction products were subjected to denaturing agarose electrophoresis and electrophoretic patterns were examined by autoradiography to evaluate recoveries of full length cDNAs and rates of short products obtained from incomplete elongation. The results are shown in Lane 1 of FIG. 2.

The reverse transcriptase Superscript II was inactivated at a temperature of 50° C. in the above standard buffer condition.

The following buffer condition for reverse transcription was used to verify that addition of oligosaccharide stabilizes the enzyme reaction: 50 mM Tris-HCl, pH 8.3, 75 mM KCl, 3 mM $MgCl_2$, 10 mM dithiothreitol, each 0.75 mM of dNTPs (DATP, dGTP, dCTP, dTTP), 20% (w/v) trehalose and 20% (v/v) glycerol.

1 µg of template RNA, 400 ng of primer (20mer SK primer) and 200 units of Superscript II were reacted in 24 µl of aqueous solution under the above buffer condition. 0.2 µl of [α-$^{32}$P]dGTP was used for labeling of reverse transcription products. Under this condition, the reverse transcriptase Superscript II exhibited higher activity than the control reaction at a normal temperature (42° C.). The primer and the template RNAs were annealed at 37° C. for 2 minutes and the enzyme activity was measured at 60° C.

Figure 2:
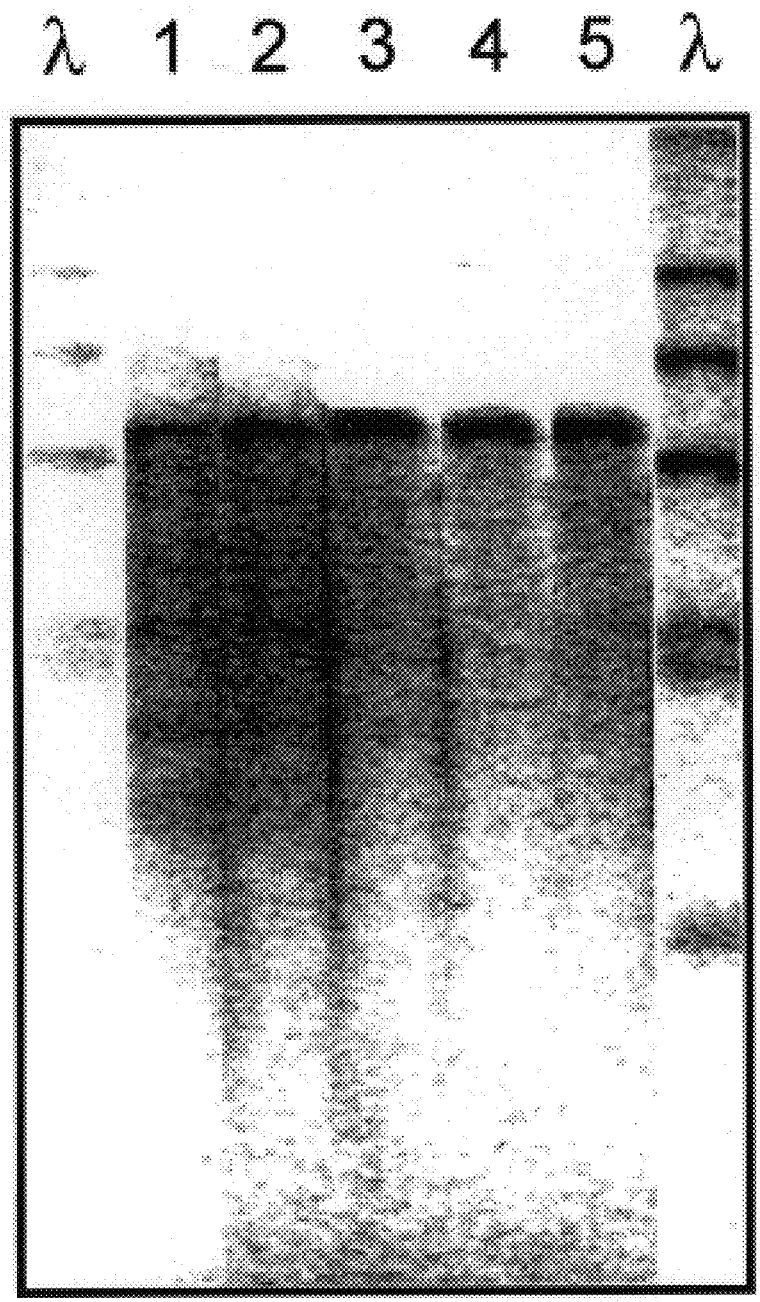
FIG. 2 is a photograph showing the results of agarose gel electrophoresis obtained in Example 2.

The reaction products were subjected to denatured agarose electrophoresis as described above, and electrophoretic patterns were examined by autoradiography to evaluate recoveries of full length cDNAs and rates of short products obtained from incomplete elongation. The results are shown in FIG. 2.

As shown in Lane 1, products resulted from premature termination of reverse transcription at specific sites or non-specific termination of reverse transcription were seen under the standard buffer condition at 42° C.

As shown in Lane 2, at 42° C. as in Lane 1, such products resulted from premature termination as mentioned above were also observed even though 20% trehalose and 20% glycerol were added.

As shown in Lane 3, when the temperature was raised to 60° C., the amount of products obtained from prematurely terminated synthesis became very small and full length products were synthesized.

As shown in Lane 5, when 0.125 μg/μl of BSA was added to the condition of Lane 3, the enzyme activity was further stabilized. However, BSA alone without 20% trehalose and 20% glycerol did not make the enzyme sufficiently heat-resistant.

As shown in Lane 4, when 0.05% of Triton X100 was added to the condition of Lane 3, the amount of incomplete reverse transcription products was further reduced. However, the whole activity of the reverse transcriptase was slightly reduced.

When the reaction was performed under the same condition as Lane 3 except that glucose or maltose was used instead of trehalose, the electrophoretic pattern showed again that the amount of products obtained from prematurely terminated synthesis became very small and full length products were synthesized.

Synthesis of CDNA from mRNA template

From the findings in the above Examples 1 and 2, it became clear that cDNAs could be synthesized with high efficiency starting from mRNAs by using the buffer condition of 50 mM Tris-HCl, pH 8.3, 75 mM KCl, 3 MM MgCl$_2$, 10 mM dithiothreitol, 0.75 mM each of dNTPs, 20% (w/v) trehalose and 20% (v/v) glycerol. The reaction conditions were as follows: 1 μg of template RNA, 400 ng of oligo-dT(12–18) primer and 200 units of Superscript II were reacted in a volume of 24 μl in the presence of [α-$^{32}$P]dGTP, the primer and the template RNAs were annealed at 37° C. for 2 minutes and the enzyme activity was measured at 60° C.

The obtained first strand cDNA chains are used in long RT-PCR or in construction of full length cDNA libraries.

Example 3

Reaction was performed under the same condition as Lane 3 of Example 2 except that arabitol, sorbitol, levulose, xylitol or betain was used instead of trehalose. The electrophoretic pattern showed again that the amount of products obtained from prematurely terminated synthesis became very small and full length products were synthesized as in Lane 3 of Example 1.

What is claimed is:

1. A method for improving heat stability of RNAs in a solution wherein the solution comprises a polyalcohol, magnesium ions, and one or more chelation agents for the magnesium ions, and wherein said chelating agents are equimolar with or in excess to the magnesium ions.

2. The method of claim 1, wherein the chelating agent comprises one or more deoxynucleotide triphosphates.

3. The method of claim 1, wherein the magnesium ions are added as MgCl$_2$.

4. The method of claim 1, wherein the heat stability is improved at a temperature of 40–100° C.

5. The method of claim 1, wherein the solution further contains more than one polyalcohol.

6. The method of claim 1, wherein the deoxynucleotide triphosphates are dATP, dCTP, dGTP, and dTTP.

* * * * *